United States Patent [19]

Krauter

[11] Patent Number: 4,934,786
[45] Date of Patent: Jun. 19, 1990

[54] WALKING BORESCOPE

[75] Inventor: Allan I. Krauter, Syracuse, N.Y.

[73] Assignee: Welch Allyn, Inc., Skaneateles Falls, N.Y.

[21] Appl. No.: 390,079

[22] Filed: Aug. 7, 1989

[51] Int. Cl.$^5$ .............................................. G02B 23/26
[52] U.S. Cl. ................................... 350/96.26; 128/4; 604/95; 604/97; 604/99; 604/101; 606/194
[58] Field of Search .................... 128/3, 4, 343, 344; 165/11.2; 604/95, 96, 97, 99, 101; 350/96.26

[56] References Cited

U.S. PATENT DOCUMENTS

| | | | |
|---|---|---|---|
| 3,485,237 | 12/1969 | Bedford | 604/95 X |
| 3,665,928 | 5/1972 | Del Guercio | 604/95 |
| 3,841,764 | 10/1974 | Snell et al. | 356/241 |
| 3,895,637 | 7/1975 | Choy | 604/95 |
| 4,148,307 | 4/1979 | Utsugi | 128/4 |
| 4,207,872 | 6/1980 | Meiri et al. | 128/4 |
| 4,389,208 | 6/1983 | LeVeen et al. | 604/95 |
| 4,769,006 | 9/1988 | Papantonakos | 604/95 |

Primary Examiner—John D. Lee
Attorney, Agent, or Firm—Wall and Roehrig

[57] ABSTRACT

An inflatable-bladder walking arrangement is provided on the outer surface of a borescope insertion tube. A pair of elongated bladders is wrapped helically over the insertion tube. This is configured such that one bladder of the pair extends radially and distally, while the other bladder when inflated expands radially and proximally. Compressed air or another flud is provided, periodically and in phase relation, to the two bladders of the pair. The bladders are inflated in alternate phase relation to move the insertion tube in a desired one of its proximal and distal directions.

10 Claims, 3 Drawing Sheets

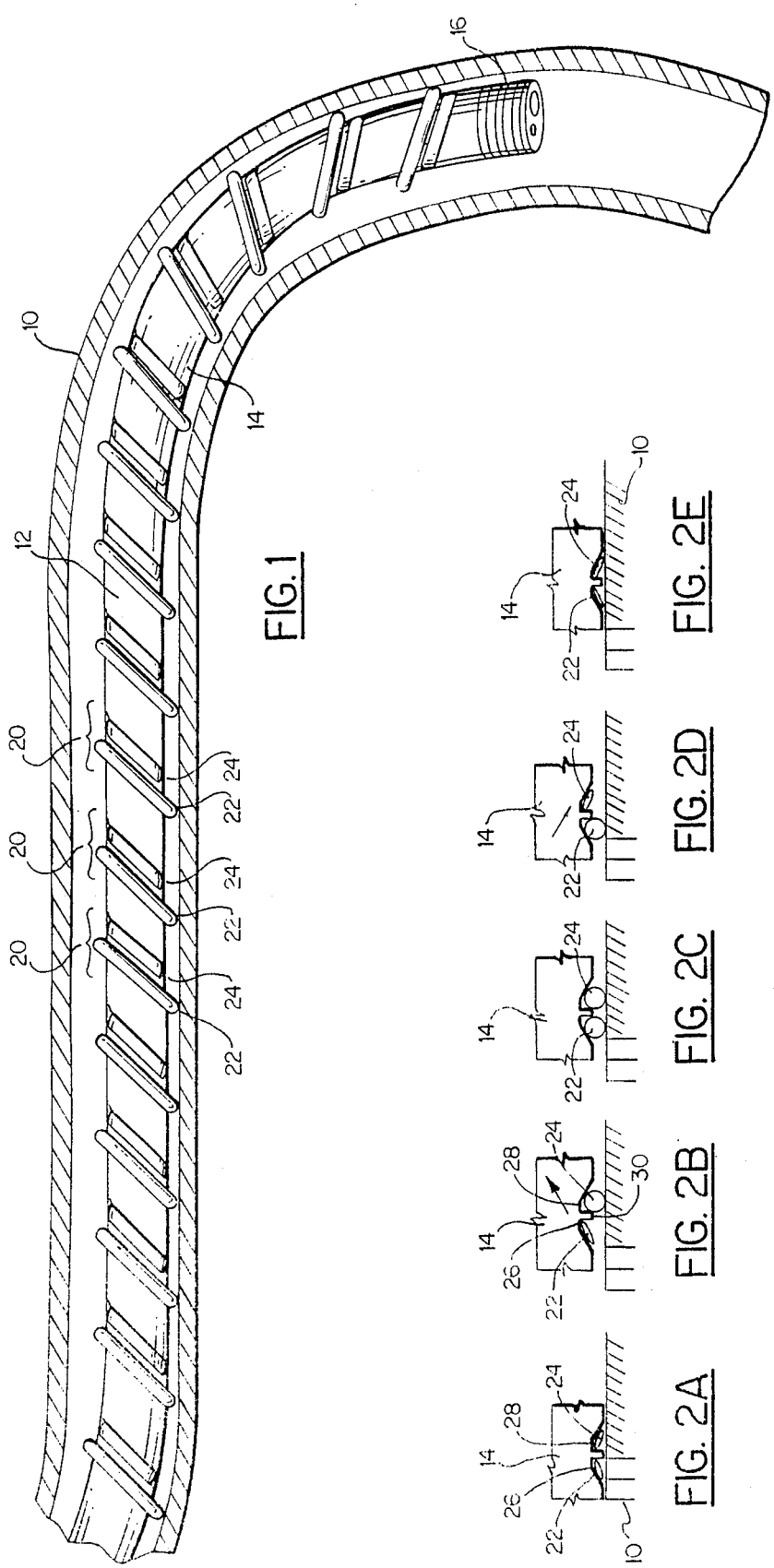

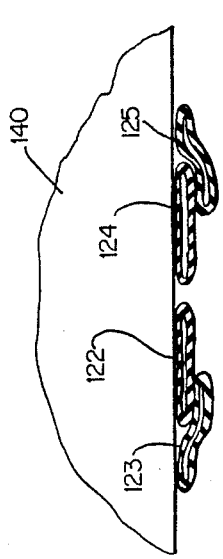
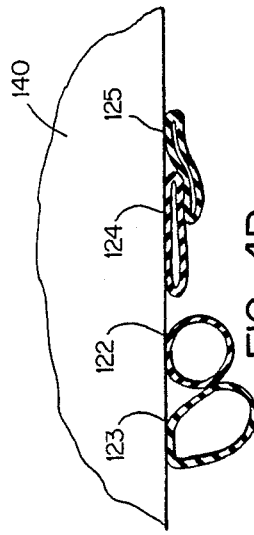
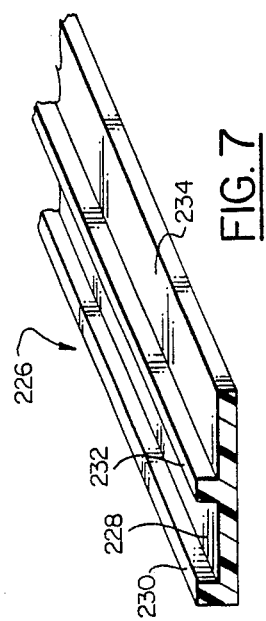
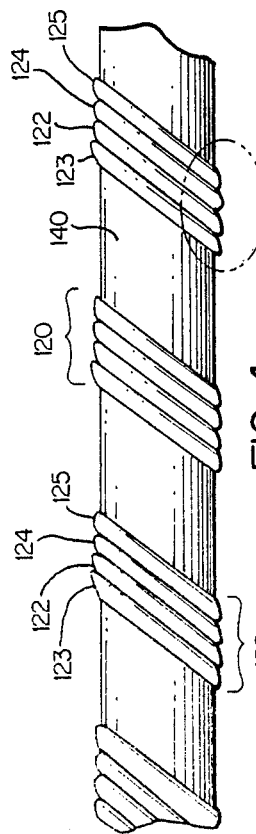
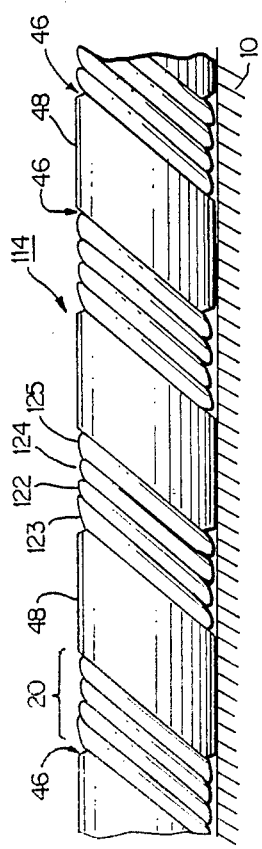
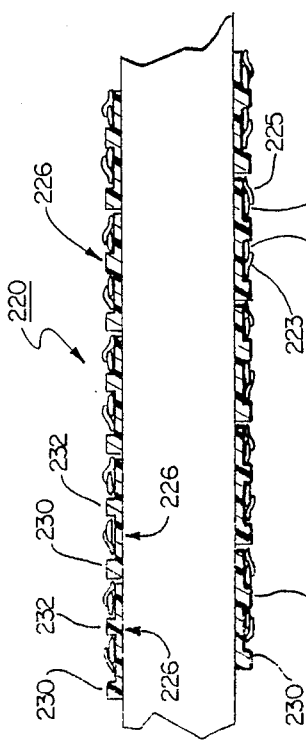

WALKING BORESCOPE

BACKGROUND OF THE INVENTION

This invention relates to flexible elongated probes, such as borescopes or endoscopes, and is more particularly directed to a system and technique for propelling an elongated flexible insertion tube within narrow, tortuous passageways.

Long industrial borescopes are extremely useful in inspecting the condition of otherwise inaccessible passages, such as boiler tubes in a steam generator or hydraulic lines in a turbine or jet engine. However, these same passageways tend to be somewhat tortuous. Consequently, because of twists and turns in the passageway, and because of friction between the sides of the insertion tube and the walls of the passageway, the distance into the passageway that the borescope insertion tube can be pushed or pulled is quite limited.

Ideally, means should be provided on the insertion tube to permit it to advance itself through passages such as curved pipes. Such means would need the following features:

axial thrust distributed along the insertion tube to avoid buckling, stretching, or excessive insertion tube-wall friction;

reversibility of movement to permit insertion or withdrawal of the insertion tube in the same manner;

controllability from the proximal end of the insertion tube;

simplicity, reliability, and low expense;

small or negligible increase in insertion tube diameter;

possibility of operation when only a part of the insertion tube is inserted into the device to be inspected; i.e., no need to install the device on the tube as the tube is being inserted;

applicability to existing insertion tubes, either permanently or as a removable option; and insensitivity to the diameter of the pipe or passageway in which the borescope insertion tube in utilized.

However, present-day insertion tubes are inserted or withdrawn only by applying force at the proximal end, distal end, or both. No one has proposed a technique which will provide the foregoing advantageous features.

Objects and Summary of the Invention

Accordingly, it is an object of this invention to provide a flexible insertion tube for a borescope, endoscope, or other similar probe with means for advancing or withdrawing the insertion tube within an elongated, narrow, and tortuous passageway, and which avoids the drawbacks of the prior art.

It is another object of this invention to provide such a technique which is relatively simple and inexpensive, and which does not significantly increase the profile of the insertion tube.

In accordance with one aspect of this invention, an elongated flexible probe has an insertion tube that is comprised of an elongated flexible tubular member and a viewing head disposed at a distal tip of the tubular member. There is at least one pair of inflatable bladders disposed in proximal-distal relation on an outer surface of a tubular member. Means are provided in association with the inflatable bladders for biasing the bladders of each pair so that, when inflated, one bladder of each pair expands radially and distally, while the other bladder of that pair expands radially and proximally. A phased and pulsed control air supply provides air to the bladders of each pair at suitable pressure, so that the bladders are inflated in sequence and with at least some degree of coincidence or overlap to move the insertion tube in the proximal direction or in the distal direction, as desired. In several preferred embodiments, the one and other of the bladders of each pair are elongated tubes which are helically wrapped onto the outer surface of the probe. The biasing means can include first and second grooves in which the one and other bladders are situated, with the grooves having a wall that slopes generally proximally for one bladder and generally distally for the other bladder. In another embodiment, the biasing is provided by a second pair of elongated flexible tube bladders that are wrapped helically on the first mentioned tubular bladders and overlying the latter on opposite sides, that is, with one of the additional pair of bladders being wrapped over a distal side of one bladder of the first pair and the other of the additional pair being wrapped over a proximal side of the other bladder of the second pair. This arrangement can be attached directly onto the outer wall of the flexible insertion tube, or within a helical recess on the insertion tube, or on an extruded flexible guide member that is wrapped helically on the tubular member. In the latter case, the flexible guide can be extruded of a plastic resin to have an F-shaped cross section.

In yet another embodiment, the bladders are arranged in an elastic sheath that is banded on to the insertion tube with one or more straps. One of the bladders is situated distally of the strap and the other is situated proximally of the strap. This sheath can be a tubular braid of metal or of a synthetic material.

The above and other objects, features, and advantages of this invention will be more fully understood from the ensuing description of a few selected preferred embodiments, and should be read in connection with the accompanying Drawing.

Brief Description of the Drawing

FIG. 1 is a view of an elongated probe incorporating this invention and situated within an elongated tubular passageway.

FIGS. 2A-2E are schematic views for explaining the general principles of this invention.

FIG. 4 shows an insertion tube according to one embodiment of this invention.

FIGS. 4A and 4B are enlargements of a portion of FIG. 4, for explaining the operation of that embodiment.

FIG. 5 shows an alternative arrangement to the embodiment of FIG. 4.

FIG. 6 is a schematic view showing an insertion tube of another embodiment of this invention.

FIG. 7 is a perspective view, partly in section, of a guide member employed in the embodiment of FIG. 6.

Detailed Description of the Preferred Embodiments

Figure 3:
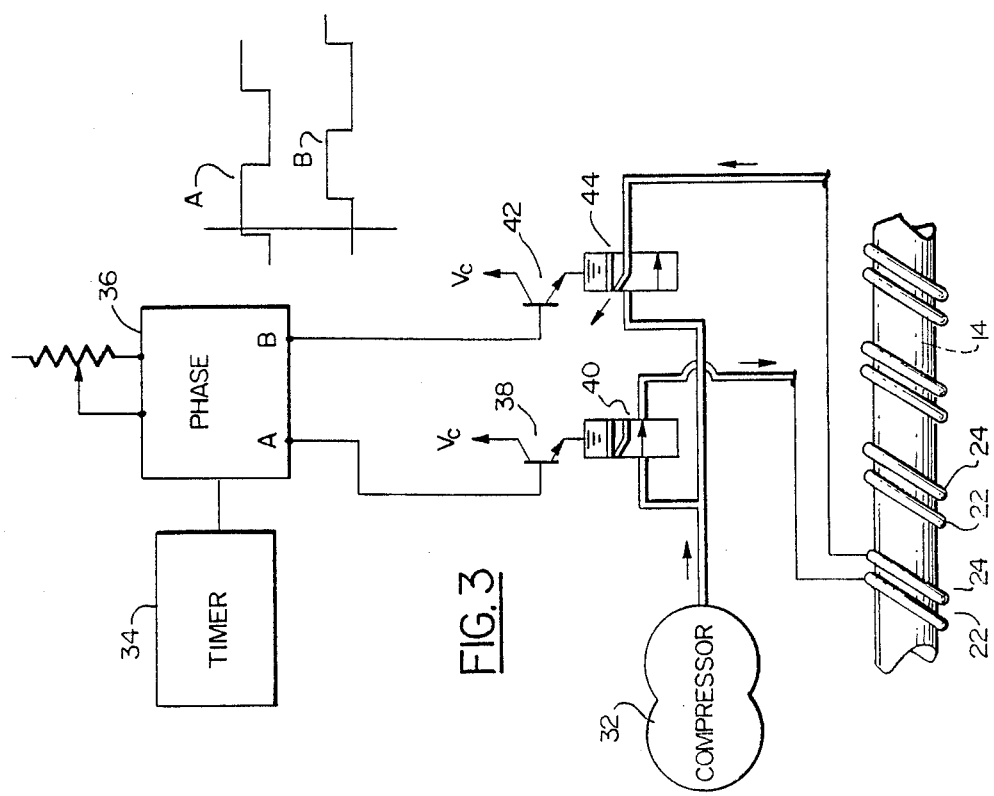
FIG. 3 is a schematic view of a pneumatic control system that can be employed with this invention.

With reference to the Drawing, FIG. 1 shows an elongated, tortuous passageway 10, which can be e.g. a hydraulic line, a heat exchanger pipe, or the like, and which is to be inspected. An elongated probe 12 or insertion tube includes an elongated flexible tubular member 14 and a video head 16 situated at the tip or distal end of the tubular member 14. Video information could also be carried back over a fiber optics bundle or through other means.

A bladder type walking arrangement 20 is situated upon the outer surface of the elongated flexible tubular member 14, and here is helically disposed thereon. The bladder type walking arrangement 20 includes at least one pair of elongated tubular inflatable bladders with one bladder 22 being oriented proximally and the other bladder 24 being oriented distally. The helical winding of the walking arrangement 20 ensures that the bladders 22 and 24 repeat themselves periodically along the length of the insertion tube, and thus appear as a multiplicity of feet.

The general operation of the invention can be simply explained with reference to FIGS. 2A-2E which show a small section of a wall of the flexible tubular member 14 on which the elongated tubular bladders 22 and 24 are situated. In the embodiment, as here depicted, there are two spiral or helical grooves 26 and 28 in which the inflatable bladders 22 and 24 are respectively situated. The groove 26 has a floor which slopes generally in the proximal direction while the groove 28 has a floor which slopes generally in the distal direction. The grooves 26 and 28 provide a sufficient recess such that, when deflated, the bladders 22 and 24 lie at or at least slightly below the surface of the tubular member 14. The groove configuration also causes that section of each bladder furthest from the center line of the tubular member 14 to move axially as well as radially during inflation.

When neither bladder 22 or 24 is inflated as in FIG. 2A, the insertion tube flexible elongated tubular member 14 rests against the inside of the tube pipe, or other passageway 10. If the distal bladder 24 is inflated, as shown in FIG. 2B, this causes the member 14 to lift radially off the passageway wall, and also to move axially by an increment as shown with reference to the index lines that appear in the Figures. After the first bladder 24 has been inflated, the other bladder 22 is inflated as shown in FIG. 2C. This causes no further movement of the tubular member 14. However, the distal bladder 24 can now be deflated as shown in FIG. 2D. Thereafter, when the proximal bladder 22 is deflated, the tubular member 14 moves both radially towards the wall of the passageway 10, and also distally by another increment, coming to rest in the position shown in FIG. 2E. This cycle is repeated continuously until the insertion tube has brought itself into the passageway 10 a desired amount.

The movement here described is entirely symmetrical: the direction of movement can be reversed simply by changing the order of inflation and deflation of the bladders 22 and 24. The inflation and deflation of the bladders 22 and 24 can be carried out with a control system of fairly straightforward design, as shown in FIG. 3. Here, a timer circuit 34 provides timing signals to a phased pulse generator 36 which provides pulse signals A and B that vary about ninety degrees in phase. The pulse A is provided to a power transistor 38 which controls a solenoid air valve 40 connected between the compressor 32 and the bladder 22, while the pulse signal B is provided through a power transistor 42 to control a solenoid valve 44 that is connected to the compressor 32 and the tubular bladder 24. The frequency and duty cycles of the pulse signals A and B can be controlled as desired for optimal operation.

One practical embodiment of this invention is shown in FIG. 4. Here, parts that correspond to elements of the previous embodiment are identified with the same reference numbers, but raised by 100. In this arrangement the bladder-type walking arrangement 120 is helically wound directly onto the outer surface of the insertion tube elongated flexible tubular member 140. This arrangement 120 includes an inner proximal tubular bladder 122 wound on the outside of the tubular member 140, with an additional tubular bladder 123 wrapped over a proximal edge of the tubular bladder 122, and an inner distal tubular bladder 124, with an additional bladder 125 wrapped over the distal edge of the bladder 124. Detail of this arrangement is shown in FIGS. 4A and 4B. Here, adhesive can be employed to attach the bladders 122-125 onto the insertion tube, but attachment can also be accomplished mechanically employing only the tension in the bladders. Here, the bladders 122 and 123 are coupled to inflate together, and the bladders 124 and 125 are also coupled to inflate together. As shown in FIGS. 4A and 4B, when the bladders 122 and 123 are inflated, the outer bladder 123 is pushed somewhat axially as well as radially which urges the insertion tube to move axially. The bladders 124 and 125, when inflated, experience motion that is the mirror image of what is shown in FIGS. 4A and 4B.

A variant of this embodiment is shown in FIG. 5. Here, the insertion tube elongated tubular member 114 has a spiral or helical cutout 46 thereon, and the tubular bladders 122, 123, 124, and 125 are situated within this cutout. The cutout 46 provides a helical land 48 situated radially outside the bladders when the latter are deflated. This structure facilitates the inserting or withdrawing of the insertion tube when the walking feature is not needed, and lowers the friction of the insertion tube relative to the passageway that is being inspected. This also reduces the possibility of damage to the bladders from sliding within a tube or pipe. A further embodiment is shown in FIGS. 6 and 7, in which parts are similar to the previous embodiments are identified by similar reference numbers, but raised by 200.

Here, for the bladder type walking arrangement 220, a helical guide 226 is helically wound onto the insertion tube, and provides a pair of channels for the tubular bladders 222, 223; and 224, 225, respectively. The channel member 226 can favorably be extruded from a flexible plastic, and have a generally F-shaped cross section, as shown in FIG. 7. A first channel 228 is defined between an edge rib 230 and a median rib 232, while a second channel 234 is defined between the median rib 232 and the edge rib 230 on the next successive wrap of the guide member 226. The guide member 226 and the bladders can be applied onto an existing borescope, and can be removed when not required.

Figure 8:
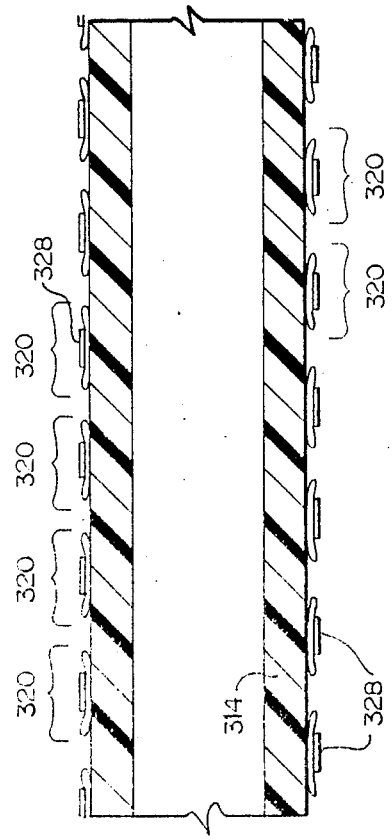
FIG. 8 shows an insertion tube according to yet another embodiment of this invention.
Figure 8A:
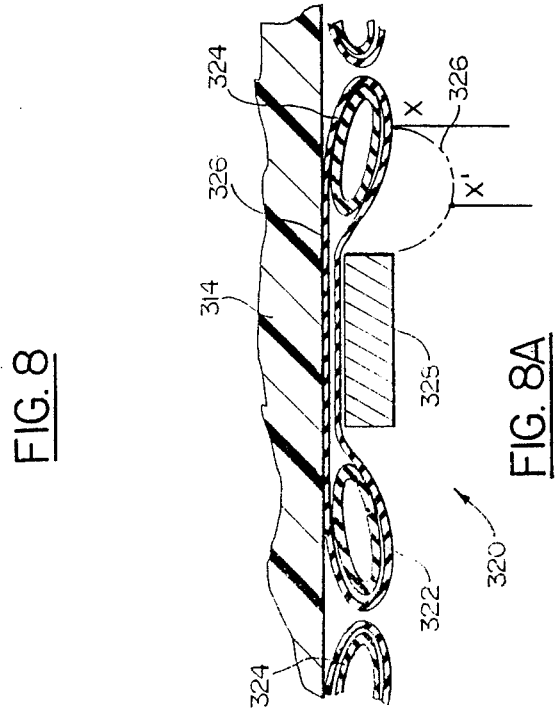
FIG. 8A is a detail sectional view of a portion of the embodiment of FIG. 8.

Still another embodiment of this invention is shown in FIG. 8. In this embodiment, a walking arrangement 320, which is shown in more detail in FIG. 8A, includes proximal and distal elongated bladders 322 and 324, with a flexible but relatively inelastic tubular sheath 326 encompassing both bladders. A strap 328 binds or clamps the bladders and sheath onto the outer wall of the insertion tube tubular member 314 in spiral fashion. This sheath can be a thin wall flexible tube, or can be a steeply angled braid of metal or of a suitable polymer. Inflating the bladders tends to expand the sheath radially outwards and also axially in the direction towards the strap 328. This motion is indicated by reference to the point X on the sheath shown in normal state (in solid line) and inflated (in ghost). Axial motion in any of these embodiments employs the same general sequence as described with respect to FIGS. 2A to 2E. The bladders for this walking borescope insertion tube arrangement need not be strictly limited to the pneumatic type, but could be inflated with a liquid or other fluid medium. While there is a circumferential (or torsional) component of motion arising from the spiral winding of the bladders, this can be resisted by the torsional stiffness of the insertion tube. Alternatively, this circumferential component can be eliminated by periodically reversing the direction of the helix, i.e. from right handed to left handed, along the insertion tube.

While the present invention has been described with respect to certain preferred embodiments, it should be recognized that the invention is not limited to those precise embodiments. Rather, many modifications and variations would present themselves to those skilled in the art without departing from the scope and spirit of this invention, as defined in the appended claims.

What is claimed is:

1. An elongated flexible probe insertion tube which comprises an elongated flexible tubular member; a viewing head disposed at a distal tip of the tubular member; at least one pair of inflatable bladders disposed in proximal-distal relation on an outer surface of said tubular member, including means for biasing said bladders of each pair such that when inflated one bladder of each pair expands radially and distally, to push distally against a surface of passageway in which the probe is inserted, and the other bladder expands radially and proximally to push proximally against the surface of the passageway; and means supplying and relieving a fluid periodically and in a two-phase relation to the one and the other bladder of each said pair so that the bladders are inflated sequentially and partially coincidentally to move the insertion tube in either one of its proximal and distal direction, as desired.

2. The elongated flexible probe of claim 1 in which said one and other bladders of each pair are elongated tubes which are helically wrapped on said outer surface.

3. The elongated flexible probe of claim 2, wherein said biasing means includes first and second grooves in which said one and other bladders are situated, said grooves each having a floor that slopes generally proximally and generally distally, respectively.

4. The elongated flexible probe of claim 1 wherein said bladders are elongated inflatable tubes wrapped helically on said outer surface of said tubular member.

5. The elongated flexible probe of claim 4 wherein said biasing means includes an additional pair of elongated flexible tube bladders wrapped helically on said tubular member and overlying the first-mentioned pair of inflatable tube bladders, one of said additional pair of bladders being wrapped over a distal side of one bladder of the first-mentioned pair and the other of said additional pair being wrapped over a proximal side of the other bladder of said first-mentioned pair, and wherein said means supplying and relieving a fluid includes means coupling the proximal one of the first-mentioned pair to the proximal one of the additional pair and means coupling the distal one of the first-mentioned pair to the distal one of the additional pair, so that the associated proximal bladders are inflated together and the associated distal bladders are inflated together.

6. The elongated tubular probe of claim 5 including an extruded flexible guide member wound helically on said tubular member and defining channels within which said first-mentioned and said additional pair of tube bladders are respectively wrapped.

7. The elongated tubular probe of claim 6 where said extruded flexible guide is of F-shaped cross section.

8. An elongated flexible probe insertion tube which comprises an elongated flexible tubular member; a viewing head disposed at a distal tip of the tubular member; at least one pair of inflatable bladders disposed in proximal-distal relation on an outer surface of said tubular member, wherein said bladders are elongated inflatable tubes wrapped helically on said outer surface of said tubular member; means for biasing said bladders of each pair such that when inflated one bladder of each pair expands radially and distally and the other bladder of the pair expands radially and proximally and means supplying and relieving a fluid periodically and in phase relation to the one and the other bladder of each said pair so that the bladders are inflated sequentially and partially coincidentially to move the insertion tube in a desired one of its proximal and distal directions; wherein said means for biasing the bladders includes a flexible but relatively inelastic sheath encompassing both of the inflatable tube bladders of said pair, and a strap banding said sheath onto said insertion tube flexible member such that one of the bladders is situated parallel to and distally of the strap and the other is situated parallel to and proximally of the strap.

9. The elongated probe of claim 8 where said sheath is a tubular braid.

10. The elongated probe of claim 8 wherein each said bladders and their relatively inelastic sheath are united or bonded to each other.

* * * * *